(12) United States Patent
Little

(10) Patent No.: US 9,937,045 B2
(45) Date of Patent: Apr. 10, 2018

(54) IMPLANTABLE PENILE PROSTHESIS INFLATION APPARATUS

(71) Applicant: AMS Research, LLC, Minnetonka, MN (US)

(72) Inventor: Eric F. Little, Shakopee, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 259 days.

(21) Appl. No.: 14/863,965

(22) Filed: Sep. 24, 2015

(65) Prior Publication Data

US 2016/0081802 A1   Mar. 24, 2016

Related U.S. Application Data

(60) Provisional application No. 62/054,472, filed on Sep. 24, 2014.

(51) Int. Cl.
*A61F 5/00* (2006.01)
*A61F 2/26* (2006.01)

(52) U.S. Cl.
CPC ..................................... *A61F 2/26* (2013.01)

(58) Field of Classification Search
CPC ......... A61F 2/26; A61F 5/41; A61F 2005/415
USPC .................................................... 600/38–41
See application file for complete search history.

(56) References Cited

U.S. PATENT DOCUMENTS 4,682,589 A * 7/1987 Finney ...................... A61F 2/26
600/40
4,917,110 A * 4/1990 Trick ........................ A61F 2/26
600/40

FOREIGN PATENT DOCUMENTS

WO         80/00302 A1    3/1980
WO     2016/049303 A1    3/2016

OTHER PUBLICATIONS

International Preliminary Report on Patentability for PCT Application No. PCT/US2015/051922, dated Apr. 6, 2017, 9 pages.
International Search Report and Written Opinion for International Application No. PCT/US2015/051922, dated Dec. 1, 2015, 12 pages.
Wikipedia, "Druckübersetzer", retrieved on Apr. 21, 2016 from https://de.wikipedia.org/wiki/Druckübersetzer, Mar. 14, 2013, 1 page.

* cited by examiner

*Primary Examiner* — John Lacyk
(74) *Attorney, Agent, or Firm* — Brake Hughes Bellermann LLP

(57) ABSTRACT

An implantable penile prosthesis inflation apparatus includes a manual pump, and a pressure amplifier. The pressure amplifier includes a first sub-amplifier having a first chamber and a piston assembly contained in the first chamber. The first chamber includes an input port that is fluidically coupled to the manual pump, and an output port. The piston assembly is configured to move along a central axis.

16 Claims, 3 Drawing Sheets

IMPLANTABLE PENILE PROSTHESIS INFLATION APPARATUS

BACKGROUND

Erectile dysfunction (ED) or impotence is the inability to get or keep an erection that is firm enough, or lasts long enough, to have successful sexual intercourse. It can have serious effects on a person's sexual relationship and their self-esteem.

Inflatable penile prostheses may be used to cure or compensate for impotence. Inflatable penile prostheses typically include a pair of inflatable cylinders and a pump. The cylinders are implanted in the corpus cavernosa of the patient, and the pump is implanted in the scrotum of the patient. For some inflatable penile prostheses (i.e., three-piece penile prostheses), a separate fluid reservoir must be implanted in the abdomen of the patient. Alternatively, the fluid reservoir may be combined with the cylinders (i.e., two-piece penile prostheses).

The cylinders of the inflatable penile prosthesis are inflated with fluid from the reservoir using the pump to produce an erect condition of the penis. The pump is often a manual pump, such as such as a single pump bulb. A patient pinches the pump bulb with his fingers to drive fluid from the reservoir into the inflatable cylinders. The fluid may be discharged from the cylinders to deflate the cylinders and produce a flaccid penis condition.

Some patients may lack the necessary dexterity and/or strength to apply sufficient pressure to the manual pump to maximize the pressurization of the inflatable cylinders by the fluid. It is, therefore, difficult for such users to place the penile prosthesis in a fully erect condition.

SUMMARY

Embodiments of the invention are directed to an implantable penile prosthesis inflation apparatus, an implantable penile prosthesis that includes the inflation apparatus, and a method of inflating a penile prosthesis cylinder. In one embodiment, the inflation apparatus includes a manual pump, and a pressure amplifier. The pressure amplifier includes a first sub-amplifier having a first chamber and a piston assembly contained in the first chamber. The first chamber includes an input port that is fluidically coupled to the manual pump, and an output port. The piston assembly is configured to move along a central axis.

One embodiment of the implantable penile prosthesis includes an inflatable cylinder having an interior chamber and an inflation apparatus. The inflation apparatus includes a manual pump, and a pressure amplifier. The pressure amplifier includes a first sub-amplifier that includes a first chamber and a piston assembly contained in the first chamber. The first chamber includes an input port that is fluidically coupled to the manual pump, and an output port that is fluidically coupled to the interior chamber of the inflatable cylinder. Actuation of the manual pump drives movement of the piston assembly along the central axis, which drives fluid into the interior chamber of the inflatable cylinder.

In one embodiment of the method of inflating an implantable penile prosthesis cylinder, a manual pump is actuated to drive a first volume of fluid into a pressure amplifier, thereby driving a second volume of fluid that is less than the first volume of fluid into an inner chamber of the penile prosthesis cylinder.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
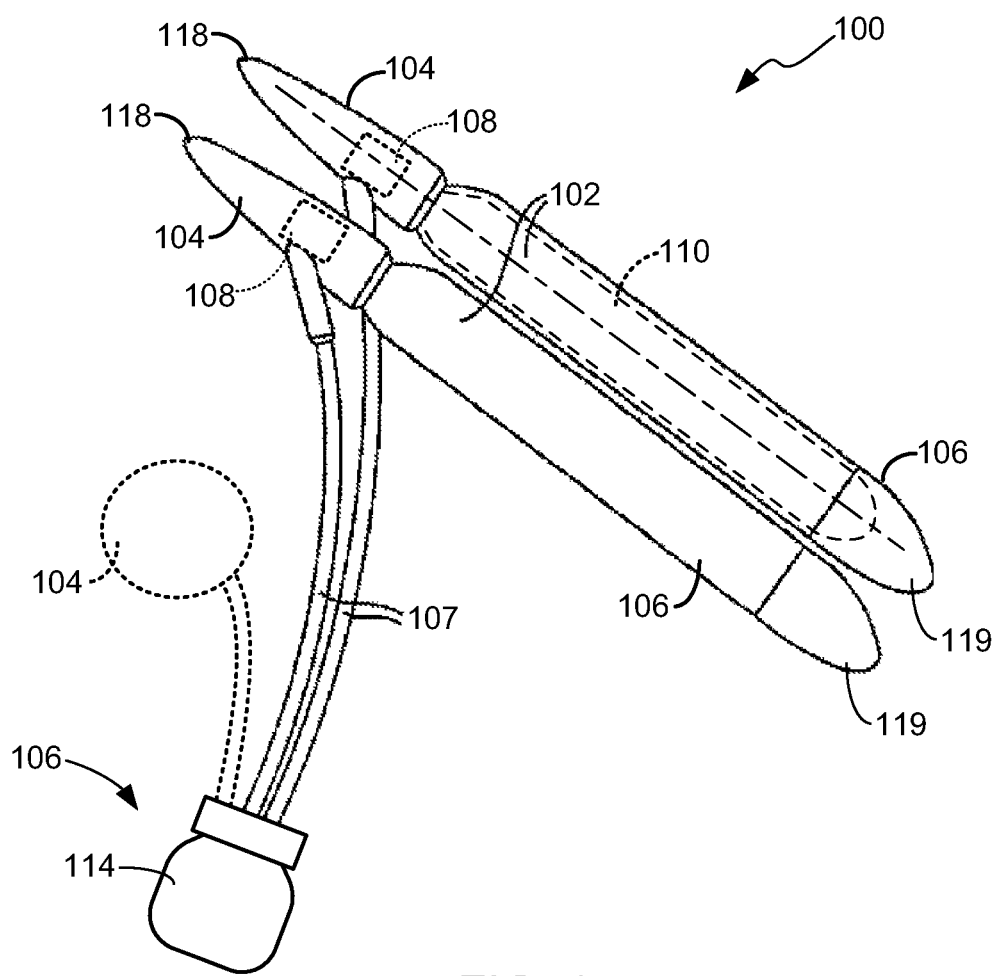
FIG. 1 is a schematic perspective view of an exemplary penile prosthesis comprising cylinders in accordance with one or more embodiments of the invention.

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present. Unless stated otherwise, embodiments of the coupled components described herein should be interpreted as including both a directly coupled embodiment and an indirectly coupled embodiment.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
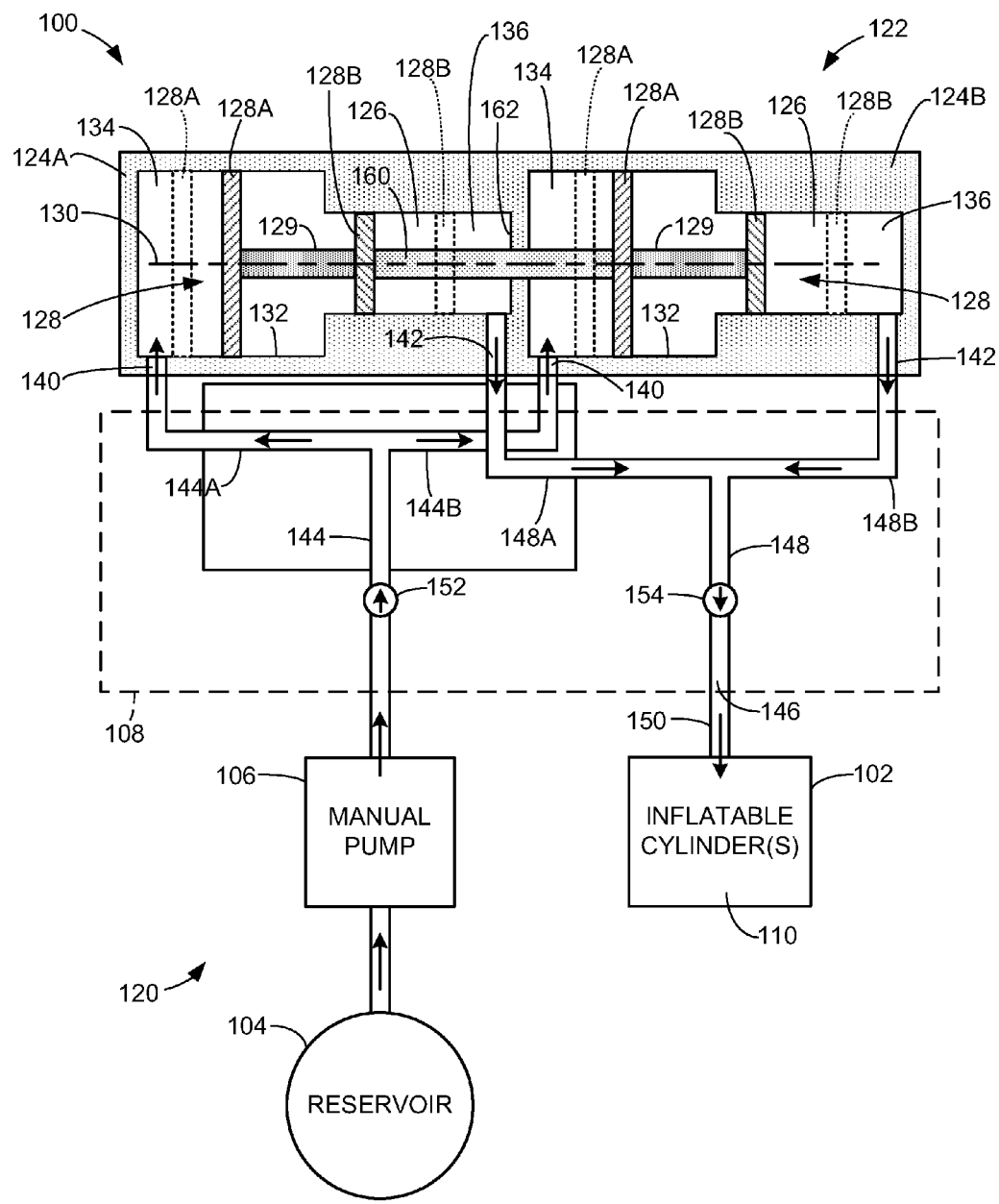
FIG. 2 is a simplified diagram of an inflation apparatus in accordance with embodiments of the invention.

FIG. 1 is a simplified perspective view of an exemplary inflatable penile prosthesis 100 in accordance with embodiments of the invention. FIG. 2 is a simplified diagram of an exemplary penile prosthesis 100 in accordance with embodiments of the invention.

In one embodiment, the penile prosthesis 100 includes a pair of inflatable cylinders 102, a fluid reservoir 104, and a manual pump 106, which may be fluidically coupled to the fluid reservoir 104 and/or the cylinders 102 through tubing 107. In some embodiments, the cylinders 102 are configured for implantation in the corpus cavernosa of a patient, and the pump 106 is configured for implantation in the scrotum, or other suitable location of the patient. In one embodiment, the fluid reservoir 104 is located at a rear portion of the cylinders 102 to form a two-piece inflatable penile prosthesis, as shown in FIG. 1. In one embodiment, the penile prosthesis 100 is in the form of a three-piece inflatable penile prosthesis, in which the fluid reservoir 104 is located externally to the cylinders 102, as indicated in phantom lines in FIG. 1, and is configured for implantation in the abdomen of the patient.

In some embodiments, the penile prosthesis 100 includes a fluid control block 108 that fluidically couples the reservoir 104 to an interior chamber 110 of the cylinders 102. Embodiments of the fluid control block 108 include fluid pathways that form fluidic connections described herein. In some embodiments, the fluid control block 108 includes one or more valves, such as one or more check valves, that control the flow of fluid through the fluid pathways.

The fluid reservoir 104 contains inflation fluid (e.g., saline), which may be driven from the fluid reservoir 104 through the fluid control block 108 and into the chambers 110 using the pump 106, to transition the penile prosthesis 100 from a deflated or flaccid condition to a rigid state corresponding to an erect penis condition. Fluid contained in the inflatable portion 106 may be returned to the reservoir 104 of the cylinder 102 through the fluid control block 108 using conventional techniques, such as by bending the cylinder 102, to deflate the cylinders 110 and transition the penile prosthesis 100 back to the flaccid condition.

Each penile prosthesis cylinder 102 may also include conventional components, such as a rear tip 118, and an end cap 119. The cylinders 102 may also comprise conventional components that are not shown in the drawings in order to simplify the illustrations. For instance, the cylinders 102 may be surrounded by an elastic (e.g., spandex) sleeve, or include other conventional components.

The manual pump 106 is configured to be actuated by the user. In one embodiment, the manual pump 106 includes a conventional pump bulb 114 (FIG. 1), which is squeezed by the fingers of the user to actuate the pump. Other manually operable pumps 106 may also be used.

In some embodiments, the fluid pressure generated in the chambers 110 of the cylinders 102 by the pump 106 is directly related to the amount of user force applied to the manual pump 106, such as the pump bulb 114, for example. Unfortunately, some users are incapable of applying sufficient force to conventional manual pumps to generate the pressure required to fully inflate the chambers 110 of the cylinders 102, such as due to dexterity or strength issues.

Some embodiments of the invention are directed to an improved inflation apparatus 120, which generally comprises the manual pump 106, and a pressure amplifier 122, exemplary embodiments of which are illustrated in FIG. 2. The pressure amplifier 122 operates to reduce the amount of force that must be applied to the manual pump 106 in order to generate sufficient fluid pressure to fully inflate the chambers 110 of the cylinders 102. As a result, embodiments of the invention overcome the deficiencies of the prior art and allow users that have difficulty applying sufficient pumping force to conventional manual pumps to more easily fully inflate the inflatable chambers 110 of the cylinders 102.

In some embodiments, the pressure amplifier 122 includes one or more sub-amplifiers, generally designated as 124, such as sub-amplifiers 124A and 124B. Each sub-amplifier 124 includes a chamber 126 and a piston assembly 128. The piston assembly 128 is contained in the chamber 126 and is supported for movement along a central axis 130 of the chamber 126 relative to the interior walls 132 forming the chamber 126.

Some embodiments of the piston assembly 128 include a piston 128A and a piston 128B. In some embodiments, the pistons 128A and 128B are joined together by a rod 129 or other suitable member, such that the pistons 128A and 128B move together along the central axis 130. The piston assembly 128 divides the chamber 126 into two sub-chambers 134 and 136. A suitable seal is formed between the interior wall 132 of the chamber 126 and the piston assembly 128 to prevent the flow of fluid between the sub-chambers 134 and 136.

In one embodiment, each sub-amplifier 124 includes an input port 140 and an output port 142. The input port 140 and the output port 142 are located on opposing sides of the piston assembly 128 with the input port 140 opening into the sub-chamber 134, and the output port 142 opening into the sub-chamber 136. The input port 140 is fluidically coupled to the manual pump component 106 through a fluid path 144. In one embodiment, the output port 142 is fluidically coupled to an output 146 through a fluid path 148. In one embodiment, the output 146 is fluidically coupled to the interior chamber 110 of the cylinders 102 through a fluid path 150, as shown in FIG. 2. In one embodiment, at least a portion of the pathways 144 and 148 are contained within the fluid control block 108, as indicated in FIG. 2. In one embodiment, the output 146 is a component of the fluid control block 108, as indicated in FIG. 2.

During an inflation operation, the piston assembly 128 is initially positioned such that the piston 128A is located near the input port 140, as indicated in phantom lines in FIG. 2. A user actuates the manual pump 106 by hand to drive fluid from the reservoir 104 through the fluid pathway 144, as indicated by the arrows in FIG. 2. This drives a volume of fluid through the input port 140 and into the sub-chamber 134 of the one or more sub-amplifiers 124. In one embodiment, the inflation apparatus 120 includes a check valve 152 in the fluid pathway 144 to prevent the backflow of the fluid toward the manual pump 106. In one embodiment, the check valve 152 may be a component of the fluid connection block 108.

As the volume of fluid is driven into the sub-chamber 134 in response to the actuation of the manual pump 106, the pressure in the sub-chamber 134 increases and drives the piston assembly 128 along the axis 130 toward the output port 142, as indicated by piston 128B drawn in phantom lines. Movement of the piston assembly 128 along the axis 130 toward the output port 142 compresses the sub-chamber 136 and drives a volume of fluid through the output port 142 and into the fluid path 148, as indicated by the arrows in FIG. 2. The fluid is driven through the fluid pathway 148 and the output 146, and into the interior chambers 110 of one or both of the cylinders 102. In some embodiments, the volume of fluid discharged from the sub-chamber 136 through the output port 142 of the one or more sub-amplifiers 124 is sufficient to fully inflate the cylinders 102 when the piston assemblies 128 move to a position adjacent the output ports 142, as indicated by the phantom piston 128B.

In some embodiments, the inflation apparatus 120 includes a check valve 154 in the fluid pathway 148 that prevents the backflow of the fluid through the output port 142 and into the sub-chamber 136 during the inflation operation. In one embodiment, the one or more check valves 154 are components of the fluid connection block 108.

In some embodiments, the pressure amplifier 122 includes multiple sub-amplifiers 124. In some embodiments, the multiple sub-amplifiers 124 include at least two sub-amplifiers, such as sub-amplifiers 124A and 124B, as shown in FIG. 2. In one embodiment, the output ports 140 of the sub-amplifiers 124A and 124B are linked to the same fluid path 144 through branches 144A and 144B, and the output port 142 of the sub-amplifiers 124A and 124B are linked to the fluid path 148 through the branches 148A and 148B, as shown in FIG. 2.

In one embodiment, the piston assemblies 128 of the sub-amplifiers 124 of the pressure amplifier 122, such as sub-amplifiers 124A and 124B, are linked together through a rod 160. In some embodiments, the rod 160 extends through a wall 162 dividing the chambers 126 of the sub-amplifiers 124A and 124B, as shown in FIG. 2. In some embodiments, a suitable seal is formed between the rod 160 and the wall 162 to prevent leakage of fluid from the sub-chamber 136 of the sub-amplifier 124A into the sub-chamber 134 of the sub-amplifier 124B. The rod 160 maintains the relative positions of the piston assemblies 128 of the sub-amplifiers 124A and 124B as the piston assemblies 128 move along the axis 130.

In some embodiments, the pressure amplifier 122 reduces the amount of pressure that must be applied by the user to the manual pump 106 to fully pressurize the cylinders 102 during the inflation operation, as compared to inflation apparatuses of the prior art. In general, the force applied to the fluid in the pathway 144 through the actuation of the manual pump 106 by the user is simultaneously applied to the pistons 128A of the piston assembly 128 of each of the sub-amplifiers 124 as a pressure P1. The applied force is equal to P1*A1, where A1 is the area of the pistons 128A. This force is equally applied to the fluid in the sub-chamber 136 by the pistons 128B. When the surface area of the piston 128B is less than the surface area A1, such as A1/X, where X is greater than 1, for example, the pressure P2 generated within the sub-chamber 136 and at the output 146 can be calculated in accordance with Equations 1 and 2.

$$P1*A1=P2*A2 \quad \text{Eq. 1}$$

$$P2=P1*A1/A2=P1*A1/(A1/X)=X*P1 \quad \text{Eq. 2}$$

Thus, when X=1, no mechanical advantage is provided by the pressure amplifier. However, when X is greater than one, a mechanical advantage is provided, in which the pressure (P2) generated in the sub-chamber 136 is the value X times greater than the pressure (P1) applied to the sub-chamber 134 in response to the actuation of the pump 106 by the user. Exemplary embodiments of the value X include 1.5, 2, 2.5, 3, 3.5, greater than 1.5, greater than 2, and greater than 3. Other values for X may also be used for the sub-amplifiers 124. In some embodiments, the value of X is different for different sub-amplifiers. For instance, the sub-amplifier 124A may have a value for X of 2, while the sub-amplifier 124B may have a value for X of 2.5. This can allow the cylinders 102 of the prosthesis 100 to have different inflated pressures and allow for the exchange of different volumes of fluid.

Thus, for a given manual force applied to the manual pump 106, a user is capable of generating higher discharge fluid pressure at the output port 142 or the output 146 than would be possible using conventional inflation apparatuses. As a result, embodiments of the inflation apparatus 120 allow a user to more fully pressurize the interior chambers 110 of the cylinders 102 than would be possible using conventional pressure apparatuses that lack the pressure amplifier 122.

Following the inflation operation, the interior chambers 110 of the cylinders 102 may be deflated to return the penile prosthesis 100 to its flaccid condition using conventional techniques. In one embodiment, a user may squeeze or bend the cylinders 102 to generate sufficient pressure within the interior chambers 110 to overcome the check valve 154 and drive fluid through the fluid pathway 148 and the output ports 142, and into the sub-chambers 136 of the one or more sub-amplifiers 124. This pressurizes the one or more sub-chambers 136 and drives the piston assemblies 128 toward the input ports 140, which in turn pressurizes the sub-chambers 134. This pressurization of the fluid in the sub-chambers 134 overcomes the check valve 152 allowing fluid to return to the reservoir 104 through the fluid pathway 144.

Some embodiments are directed to a method of inflating an implantable penile prosthesis cylinder 102 using the inflation apparatus 120 formed in accordance with one or more embodiments described herein. In some embodiments of the method, the manual pump 106 is actuated to drive a volume of fluid into the pressure amplifier 122, thereby driving a volume of fluid into the interior chamber 110 of the cylinder 102 to inflate the cylinder 102. In some embodiments, the actuation of the manual pump 106 drives the volume of fluid into the pressure amplifier 122 at a first pressure that is lower than the pressure at which the volume of fluid is driven into the interior chamber 110 of the cylinder 102. As a result, the interior chamber 110 of the cylinder may be inflated to a higher pressure than that generated by the user's actuation of the manual pump 106.

Figure 3:
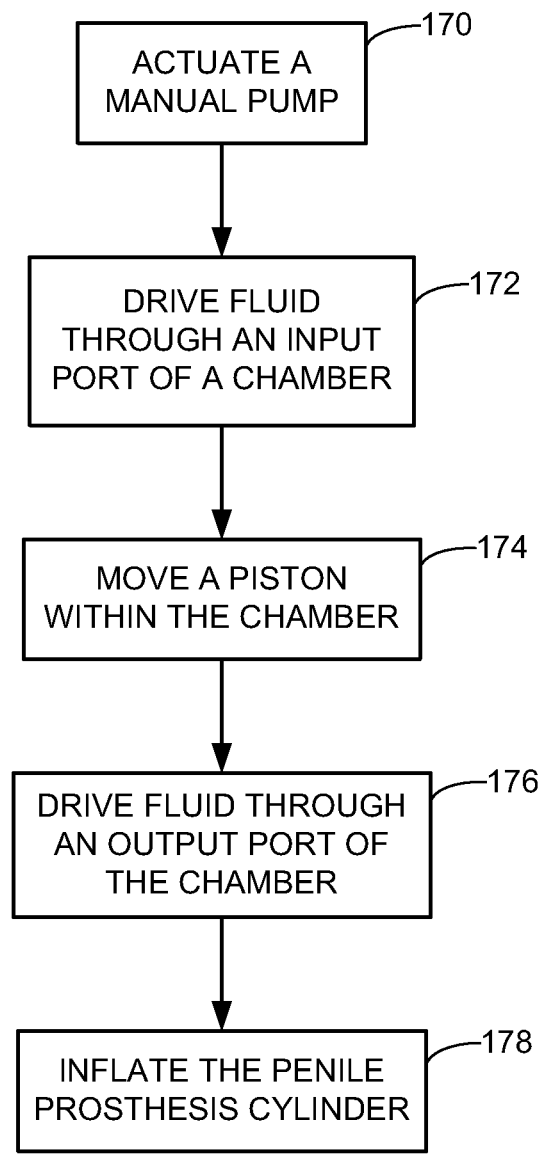
FIG. 3 is a flowchart illustrating a method of inflating an implantable penile prosthesis cylinder in accordance with embodiments of the invention.

FIG. 3 is a flowchart illustrating an exemplary method of inflating an implantable penile prosthesis cylinder 102 in accordance with more specific embodiments of the invention.

At 170 of the method, a manual pump, such as the manual pump 106, is actuated by a user. In some embodiments, the manual pump 106 includes a pump bulb that is manually actuated by the user.

At 172 of the method, fluid is driven through an input port 140 of a chamber 126 of a sub-amplifier 124 in response to the actuation of the manual pump in step 170. In some embodiments of step 172, fluid may be driven into the input ports 140 of multiple sub-amplifiers 124, such as sub-amplifiers 124A and 124B shown in FIG. 2.

At 174, a piston assembly 128 is moved within the chamber 126 in response to step 172, as discussed above. In some embodiments, when multiple sub-amplifiers are used, multiple pistons 128 may move within their respective chambers 126 in response to step 172.

At 176 of the method, fluid is driven through an output port 144 of the chamber 126 in response to step 174, as discussed above. In some embodiments, when multiple sub-amplifiers 124 are used by the inflation apparatus 120, step 176 involves the driving of fluid through the output ports of each of the sub-amplifiers 124, as discussed above.

At 178 of the method, the penile prosthesis cylinder 102 is inflated in response to step 176. In some embodiments, step 178 involves the inflation of two penile prosthesis cylinders 102 in response to step 176.

In some embodiments, steps 172 and/or 178 involve the driving of fluid through a fluid connection block 108, as discussed above.

Following the inflation process illustrated in FIG. 3, the one or more penile prosthesis cylinders 102 may be deflated as discussed above. In some embodiments, the deflation of the one or more penile prosthesis cylinders 102 involves pressurizing the cylinders 102 to overcome check valves, such as check valves 152 and 154 (FIG. 2) to drive fluid out of the cylinders 102, as discussed above.

Although the present invention has been described with reference to preferred embodiments, workers skilled in the art will recognize that changes may be made in form and detail without departing from the spirit and scope of the invention. For example, while the exemplary embodiments described herein focus on single- or multi-chamber pressure amplifiers, any suitable amplifier mechanism may be used in the embodiments of the invention.

What is claimed is:

1. An implantable penile prosthesis inflation apparatus comprising:
   a reservoir configured to hold fluid;
   at least one cylinder including an interior chamber;
   a manual pump fluidically coupled to the reservoir;
   a pressure amplifier including a first chamber, a second chamber, and a seal configured to substantially prevent a flow of fluid between the first chamber and the second chamber, each of the first chamber and the second chamber having an input port that is fluidically coupled to the manual pump, and an output port that is fluidically coupled to the interior chamber; and
   a piston assembly configured to move along a central axis of the pressure amplifier, the piston assembly having at least one first piston disposed within the first chamber and at least one second piston disposed within the second chamber.

2. The apparatus according to claim 1, wherein the at least one first piston is disposed between the input port of the first chamber and the output port of the first chamber.

3. The apparatus according to claim 1, further comprising a fluid connection block fluidically coupling the input port of the first chamber to the manual pump, and the output port of the first chamber to an output of the fluid connection block.

4. The apparatus according to claim 1, wherein the at least one second piston is disposed between the input port of the second chamber and the output port of the second chamber.

5. The apparatus according to claim 1, further comprising a fluid connection block that fluidically couples the input ports of the first and second chambers to the manual pump, and fluidically couples the output ports of the first and second chambers to an output of the fluid connection block.

6. The apparatus according to claim 1, wherein the piston assembly includes a rod connecting the at least one first piston disposed within the first chamber and the at least one second piston disposed within the second chamber, the piston assembly configured to move along the central axis relative to the input and output ports of the first and second chambers.

7. The apparatus according to claim 5, further comprising:
   a first fluid path connecting the input ports of the first and second chambers to an input of the fluid connection block; and
   a second fluid path connecting the output ports of the first and second chambers to the output of the fluid connection block.

8. The apparatus according to claim 1, wherein the at least one first piston includes two pistons having different sizes.

9. An implantable penile prosthesis comprising:
   a reservoir configured to hold fluid;
   an inflatable cylinder having an interior chamber;
   a manual pump;
   a pressure amplifier including a first chamber, a second chamber, and a seal configured to substantially prevent a flow of fluid between the first chamber and the second chamber, each of the first chamber and the second chamber having an input port that is fluidically coupled to the manual pump, and an output port that is fluidically coupled to the interior chamber of the inflatable cylinder; and
   a piston assembly having at least one first piston disposed within the first chamber and at least one second piston disposed within the second chamber,
   wherein actuation of the manual pump is configured to drive movement of the piston assembly along a central axis of the pressure amplifier, which drives fluid into the interior chamber of the inflatable cylinder.

10. The penile prosthesis according to claim 9, wherein the at least one first piston is disposed between the input port of the first chamber and the output port of the second chamber.

11. The penile prosthesis according to claim 9, further comprising a fluid connection block fluidically coupling the input port of the first chamber to the manual pump, and the output port of the first chamber to an output of the fluid connection block.

12. The penile prosthesis according to claim 9, wherein the piston assembly include a rod connecting the at least one first piston disposed within the first chamber and the at least one second piston disposed within the second chamber, the piston assembly configured to move along the central axis relative to the input and output ports of the first and second chambers.

13. The penile prosthesis according to claim 9, wherein the at least one first piston includes two pistons having different sizes.

14. A method of inflating an implantable penile prosthesis cylinder comprising:
   actuating a manual pump;
   driving at least portion of a first volume of fluid into an input port of a first chamber of a pressure amplifier in response to the actuating the manual pump, the pressure amplifier including a second chamber separate from the first chamber;
   moving at least one piston of a piston assembly within the first chamber along a central axis in response to the portion of the first volume of fluid being driven through the input port;
   driving at least a portion of a second volume of fluid through an output port of the first chamber in response to the movement of the at least one piston within the first chamber; and inflating an interior chamber of the penile prosthesis cylinder with at least the portion of the second volume of fluid being driven through the output port.

15. The method according to claim 14, wherein a pressure of the portion of the first volume of fluid driven through the input port is less than a pressure of the portion of the first volume of fluid driven through the output port.

16. The method according to claim 14, wherein the at least one piston is a first piston, the piston assembly including a second piston, the method further comprising:
   driving at least a portion of the first volume fluid through an input port of the second chamber of the pressure amplifier in response to actuating the manual pump;
   moving the second piston within the second chamber in response to the portion of the second volume of fluid being driven through the input port of the second chamber;
   driving at least a portion of the second volume of fluid through an output port of the second chamber in response to the movement of the second piston within the second chamber; and
   inflating the interior chamber of the penile prosthesis cylinder with at least the portion of the second volume of fluid being driven through the output port of the second chamber.

* * * * *